United States Patent [19]

Gray

[11] Patent Number: 5,508,279
[45] Date of Patent: Apr. 16, 1996

[54] METHODS AND COMPOSITIONS OF (+) DOXAZOSIN FOR THE TREATMENT OF BENIGN PROSTATIC HYPERPLASIA

[75] Inventor: Nancy M. Gray, Marlboro, Mass.

[73] Assignee: Sepracor, Inc., Marlborough, Mass.

[21] Appl. No.: 206,764

[22] Filed: Mar. 7, 1994

Related U.S. Application Data

[63] Continuation of Ser. No. 970,685, Nov. 4, 1992, abandoned.

[51] Int. Cl.$^6$ .................................................. A61K 31/495
[52] U.S. Cl. ........................................................... 514/254
[58] Field of Search .............................................. 514/254

[56] References Cited

U.S. PATENT DOCUMENTS

| | | | |
|---|---|---|---|
| 4,188,390 | 2/1980 | Campbell | 424/251 |
| 5,212,176 | 5/1993 | Kyncl et al. | 514/254 |

OTHER PUBLICATIONS

"Doxazosin—A Review of Its Pharmacodynamic and Pharmacokinetic . . ." Young et al. *Drug Evaluation* 35 525–541 (1988).
"Optimisation of Chiral Separation of Doxazosin Enantiomers by High–Performance Liquid Chromatography on a Second Generation $\alpha_1$–Acid Glycoprotein Column" Ley et al. *Recent Advances in Chiral Separations* 97–103 (1991).
"A Pharmacodynamic and Pharmacokinetic Assessment of a New $\alpha$–Adrenoceptor Antagonist, Doxazosin (UK33274) In Normotensive Subjects" Elliott et al. *Br. J. Clin. Pharmac.* 13 669–703 (1982).
"Scrip's New Product Review No. 12 Doxazosin" No Author *PJB Publications Ltd.* 1–17 (1986).
"Mechanisms Contributing to the Arrhythmogenic Influences of Alpha$_1$–Adrenergic Stimulation in the Ischemic Heart" Corr et al. *Am. J. of Med.* 87 19S–25S (1989).
"Subtypes of $\alpha_1$– and $\alpha$–Adrenergic Receptors" Bylund *FASEB J.* 6 832–839 (1992).
"Effects of Prazosin in Patients With Benign Prostatic Obstruction" Hedlund et al. *J. of Urol.* 130 275–278 (1982).
"Concentration and Composition of Lipoproteins in Blood Plasma of the WHHL Rabbit" Havel et al. *Arteriosclerosis* 2 467–474 (1982).
"Double–blind Comparison of the Effects of Long–term Treatment with Doxazosin or Atenolol on Serum Lipoproteins" Lehtonen et al. *Brit. J. Clin. Pharmac.* 21 77S–81S (1986).
"Multicentre 12–week Double-bind Comparison of Doxazosin, Prazosin and Placebo in Patients with Mild to Moderate Essential Hypertension" Torvik et al. *Brit. J. Clin. Pharmac.* 21 69S–75S (1986).
Owens et al. "The effect of alpha blockade on cholesterol regulation in vitro and in vivo." *Biochem. Soc. Trans.*, 20(4), 342S (1992).
Hernandez et al. "Evidence of an antiplatelet aggregation action of doxazosin in patients with hypertension: An ex vivo study" *Am. Heart J.* 121, 395–401 (1991).
Kowala et al. "Doxazosin and cholestyramine similarly decrease fatty streak formation in the aortic arch of hyperlipidemic hamsters" *Atherosclerosis* 91, 35–49 (1991).
Pool et al. "Alpha$_1$–adrenoreceptor blockade and the molecular basis of lipid metabolism alterations" *J. Human Hypertens.* 4, 23–33 (1990).
Mandal and Vaidyanathan "Non–Operative Management of Symptomatic Benign Prostatic Hyperplasia" *Indian J. Urol.* 6, 45–48 (1990).
Chapple "Medical Treatment for Benign Prostatic Hyperplasia" *Brit Med. J.* 304, 1198–1199 (1992).
Chapple et al. "Longer–Term Experience With A Permanently Implanted Prostatic Stent", *Neurourology and Urodynamics* 10, 308–309 (1991).
"2,4–Diamino–6,7–dimethoxyquinazolines. 1. 2–[4–(1, 4–Benzodioxan–2–ylcarbonyl)piperazin–1–yl] Derivatives as $\alpha_1$–Adrenoceptor Antagonists and Antihypertensive Agents" Campbell et al. *J. Med. Chem.* 30, 39–57 (1987).
"Stereoselectivity in pharmacodynamics and pharmacokinetics" Ariëns *Schweiz. Med. Wochenschr.* 120, 131–134 (1990).
"Racemische therapeutica probleemmiddelen" Ariëns *Pharm. Weekblad* 125(22) 552–554 (1990).
"Racemates Versus Enantiomers in Drug Development: Dogmatism or Pragmatism?" Testa et al. *Chirality* 2 129–133 (1990).
"Racemic therapeutics—ethical and regulatory aspects" Ariëns *Eur. J. Clin. Pharmacol.* 41 89–93 (1991).
"Prostataadenom: Neue Arzneimittel, neue Operationstechniken" Heinzl *Med. Monatsschr. Pharm.* 15 362–364 (1992).
"Binding and Functional Properties of Doxazosin in the Human Prostate Adenoma and Canine Brain" Lepor et al. *Prostate* 16 29–38 (1990).

*Primary Examiner*—Marianne M. Cintins
*Assistant Examiner*—William R. A. Jarvis
*Attorney, Agent, or Firm*—Heslin & Rothenberg

[57] ABSTRACT

Methods are disclosed utilizing the optically pure (+) isomer of doxazosin. This compound is a potent drug for the treatment of benign prostatic hyperplasia while avoiding the concomitant liability of hypotensive effects associated with the racemic mixture of doxazosin.

8 Claims, No Drawings

METHODS AND COMPOSITIONS OF (+) DOXAZOSIN FOR THE TREATMENT OF BENIGN PROSTATIC HYPERPLASIA

This application is a continuation of application Ser. No. 07/970,685, filed Nov. 4, 1992, now abandoned.

BACKGROUND OF THE INVENTION

This invention relates to novel compositions of matter containing optically pure (+) doxazosin. These compositions are of utility in the treatment of patients with benign prostatic hyperplasia (BPH) or in the treatment of patients with elevated serum low density lipoprotein (LDL) levels. Pure (+) doxazosin exhibits little of the hypotensive activity associated with the (−) enantiomer and is therefore superior to racemic doxazosin for these indications. Also disclosed are methods for treating BPH and elevated LDL in a human while avoiding the hypotensive effects that are associated with the racemic mixture of doxazosin by administering the (+) isomer of doxazosin to said human.

The active compound of these compositions and methods is an optical isomer of doxazosin, which is described by Young and Brogden in Drugs 35, 525–541 (1988) and U.S. Pat. No. 4,188,390. Chemically, the active compound is the (+) isomer of 4-amino-2-[4-(1,4-benzodioxan-2-carbonyl)piperazin-1-yl]-6,7-dimethoxyquinazoline also known as 1-(4-amino-6,7-dimethoxy-2-quinazolinyl)-4-[(2,3-dihydro-1,4-benzodioxan-2-yl)carbonyl]piperazine hereinafter referred to as doxazosin.

(+) Doxazosin, which is the subject of the present invention, is available commercially only as the 1:1 racemic mixture. That is, (+) doxazosin is available only as a mixture of optical isomers, called enantiomers. The racemic mixture of doxazosin is commercially available for administration as a methanesulfonate (mesylate) salt, but extensive pharmacology has been published on the hydrochloride salt as well.

Many organic compounds exist in optically active forms, i.e. they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. There is no correlation between nomenclature for the absolute stereochemistry and for the rotation of an enantiomer. Thus, D-lactic acid is the same as (−) lactic acid, and L-lactic acid is (+). For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Doxazosin (I) is a representative of a group of drugs that block $\alpha_1$ adrenoceptors. $\alpha_1$ Receptors are innervated by postganglionic sympathetic neuronal fibers and are located in many body systems, including the cardiovascular system and the urinary tract. Evidence is now beginning to accumulate that there are subtypes of $\alpha_1$ receptors, making $\alpha_1$ adrenergic receptors a family of recognition units rather than a monolithic element. Bylund [FASEB J. 6, 832–839 (1992)] has presented evidence that there are at least three presently differentiable $\alpha_1$ receptor subtypes. Prazosin (II), an achiral analog of doxazosin, is reported to have similar affinities for each of these subtypes.

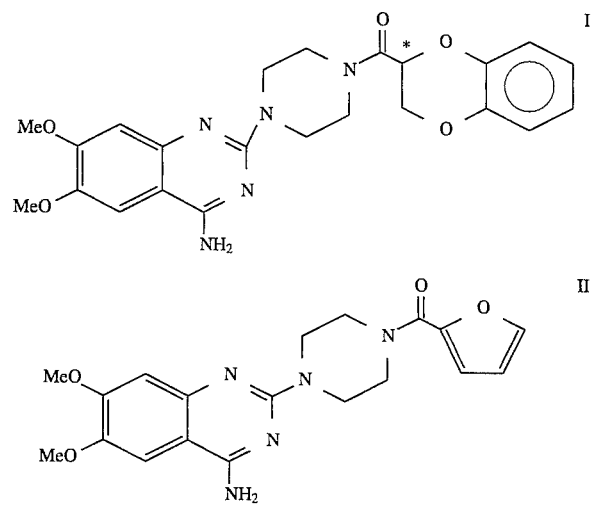

Doxazosin has a single chiral center located on the carbon adjacent to the carboxyl group (shown in formula I). This gives rise to a pair of enantiomers which have been resolved by Ley et al. [Recent Advances in Chiral Separations, Steven and Wilson Editors, Plenum Press, New York (1991) pages 97–103] on an analytical scale (0.52 μg), but there are no reports in the literature of a preparative-scale separation of the enantiomers.

Although the inventor does not wish to be bound by a theoretical construct, it is possible that the beneficial effects of (+) doxazosin in increasing urine flow and bladder evacuation and in improving serum lipid profiles with minimal effects on such other cardiovascular parameters as blood pressure and heart rate arise from the selective inhibition of a specific subset of $\alpha_1$ receptors by the (+) isomer as compared to its enantiomer, which may preferentially inhibit those subsets involved in regulating blood pressure.

The racemic mixture of doxazosin is presently used primarily as an antihypertensive agent. Doxazosin's oral bioavailability is good and the plasma half life in man is approximately 10 hours following both oral and intravenous administration. There are reports that the administration of racemic doxazosin leads to modestly decreased total cholesterol and LDL levels. [Young & Brogden Drugs 35, 525–541 (1988) and references therein.] There is also a report of the use of prazosin (II) to treat BPH [Hedlund et al., J. Urology 130, 275–278 (1983)]. However, neither of the drugs has enjoyed widespread use for either BPH or improvement of serum lipid profiles because of the cardiovascular effects that are the primary result of their administration.

A troublesome cardiovascular problem related to the use of previously known $\alpha_1$ receptor antagonists for the treatment of BPH and the improvement of serum lipid profiles is their hypotensive activity, which is particularly reflected in the problem of orthostatic hypotension. Symptomatic orthostatic hypotension is most likely to occur with high initial doses of earlier $\alpha_1$ antagonists or may occur when the dose is increased rapidly. A modest degree of fluid retention, which is another result of vasodilation, may be observed. Reflex tachycardia is also occasionally observed.

Many of the $\alpha_1$ antagonists cause somewhat similar adverse effects. The incidence of reported side effects associated with racemic doxazosin-treated patients has varied among studies. The incidence of total side effects associated with doxazosin in patients treated for hypertension has ranged between 0 and 75%, but has generally been similar to that seen with other $\alpha_1$-blocking agents at dosages producing a similar reduction in blood pressure. The most frequently reported side effects have been postural hypotension, nausea, lethargy, fatigue and dizziness.

It would be particularly desirable to find an $\alpha_1$ antagonist that exhibited the beneficial effect on serum lipids hinted at by the racemic mixture of doxazosin but which would not have effects on blood pressure and heart rate. It would also be desirable to find a superior and selective $\alpha_1$ antagonist for the treatment of BPH.

SUMMARY OF THE INVENTION

It has now been discovered that the optically pure (+) isomer of doxazosin is an effective agent for the treatment of BPH that avoids the hypotensive effects of racemic doxazosin. It is also an effective agent for the improvement of serum lipid profiles that avoids the adverse effects associated with the administration of the racemic mixture. The present invention also includes methods for treating BPH and for treating or preventing atherosclerosis in a human while avoiding the cardiovascular effects that are associated with the racemic mixture of doxazosin, by administering the optically pure (+) isomer of doxazosin to said human.

DETAILED DESCRIPTION OF THE INVENTION

The present invention encompasses a method of eliciting an increase in urine flow in a human, while avoiding the concomitant liability of hypotensive effects associated with the administration of racemic doxazosin, which comprises administering to a human an amount of (+) doxazosin, or a pharmaceutically acceptable salt thereof, substantially free of its (−) stereoisomer, said amount being sufficient to increase urine flow, but insufficient to cause the hypotensive effects associated with the racemic mixture of doxazosin.

The present invention also encompasses a composition for increasing urine flow in a human, which comprises an amount of (+) doxazosin, or a pharmaceutically acceptable salt thereof, substantially free of its (−) stereoisomer, said amount being sufficient to increase urine flow but insufficient to cause the hypotensive effects associated with racemic doxazosin.

The present invention also encompasses a method of lowering plasma cholesterol and low density lipoprotein levels in a human while avoiding the concomitant liability of adverse effects associated with racemic doxazosin, which comprises administering to a human an amount of (+) doxazosin, or a pharmaceutically acceptable salt thereof, substantially free of its (−) stereoisomer, said amount being sufficient to lower the cholesterol and LDL levels but insufficient to cause the adverse effects associated with racemic doxazosin.

The present invention also encompasses a composition for lowering serum cholesterol and low density lipoprotein in humans, which comprises an amount of (+) doxazosin or a pharmaceutically acceptable salt thereof, substantially free of its (−) stereoisomer, said amount being sufficient to lower serum low density lipoproteins, but insufficient to cause adverse effects associated with the administration of racemic doxazosin.

The available racemic mixture of doxazosin (i.e. a 1:1 racemic mixture of the two enantiomers) possesses antihypertensive activity and provides therapy and a reduction of symptoms in conditions and disorders related to hypertension. In addition, racemic doxazosin has been shown to improve the profile of serum lipoproteins in humans. Epidemiological studies have indicated that high concentrations of high density lipoprotein (HDL) cholesterol are a negative risk factor for coronary artery disease, while high concentrations of low density lipoprotein (LDL) cholesterol are a positive risk factor. During doxazosin administration to hypertensive patients there has been a trend to an increase in high density lipoprotein cholesterol and in HDL/total cholesterol ratio and to a decrease in plasma total cholesterol and triglycerides. Changes relative to baseline were occasionally significant for HDL/total cholesterol ratio, triglycerides and total cholesterol. The effect was evident after 12 weeks' treatment and was maintained for up to 1 year. Unfortunately, the strong hypotensive effects of racemic doxazosin make the presently available drug unattractive for the purpose of improving lipoprotein profiles in the prevention and treatment of coronary artery disease. The use of the substantially pure (+) isomer makes possible the desired favorable effect on serum lipoprotein profiles while eliciting diminished cardiovascular activity. "Cardiovascular" activity encompasses hypotension, vasodilation, tachycardia, and increased cardiac output.

The smooth muscles of the human bladder neck, bladder base, urethra and prostatic capsule are innervated sympathetically, and contraction-mediating $\alpha$-adrenoceptors have been demonstrated in these structures. It has been suggested that urinary retention as the result of increasing outflow obstruction in benign prostatic hyperplasia may be caused partly by stimulation of prostatic $\alpha$-adrenoceptors. Supporting this view, favorable results have been reported during treatment with the $\alpha$-adrenoceptor blockers phenoxybenzamine and prazosin.

Isolated human urethra contracted by noradrenaline is relaxed completely by prazosin. Furthermore, prazosin exerts an $\alpha$-adrenoceptor blocking effect on both human prostatic adenoma tissue and prostatic capsule tissue in vitro. Thus, if stimulation of $\alpha$-adrenoceptors contributes to the obstruction of benign prostatic hyperplasia, their blockade ought to be effective therapeutically, and, in fact, prazosin has been shown to improve urinary flow and bladder evacuation in patients suffering from benign prostatic hyperplasia. There are no reports of the use of doxazosin for this indication. The use of substantially pure (+) doxazosin makes possible the improvement in urinary flow and bladder evacuation without the concomitant cardiovascular activity of classical $\alpha_1$ antagonists and racemic doxazosin. It is therefore, more desirable to administer the (+) isomer of doxazosin than racemic doxazosin.

The term "adverse effects" includes, but is not limited to hypotension, postural hypotension, nausea, lethargy, fatigue and dizziness. Side effects that have been reported with doxazosin include headache, blurred vision, edema, chest discomfort, constipation, dry mouth, sexual dysfunction, anxiety or nervousness, insomnia, palpitations, tachycardia, rash, paresthesia, muscle cramps, increased sweating, conjunctivitis, diarrhea, flatulence, dyspnea, leukopenia, neutropenia, rhinitis and increased frequency of micturition.

The term "substantially free of its (−) stereoisomer" as used herein means that the compositions contain a greater proportion of the (+) isomer of doxazosin in relation to the (−) isomer. In a preferred embodiment, the term "substantially free of its (−) isomer" as used herein means that the composition is at least 90% by weight of (+) doxazosin and 10% by weight or less of (−) doxazosin. In a more preferred embodiment the term "substantially free of the (−) stereoisomer" means that the composition contains at least 99% by weight of (+) doxazosin, and 1% or less of (−) doxazosin. In the most preferred embodiment, the term "substantially free of its (−) stereoisomer" as used herein means that the composition contains greater than 99% by weight of (+) doxazosin. These percentages are based upon the total amount of doxazosin in the composition. The terms "substantially optically pure (+) isomer of doxazosin or "substantially optically pure (+) doxazosin" and "optically pure (+) isomer of doxazosin and "optically pure (+) doxazosin" are also encompassed by the above-described amounts.

The chemical synthesis of the racemic mixture of doxazosin can be performed by the method described in U.S. Pat. No. 4,188,390. The individual enantiomers of doxazosin may be obtained by resolution of the racemic mixture of enantiomers using conventional means. Doxazosin may be resolved with an optically active acid such as tartaric acid at the N-(1,4-benzodioxan-2-carbonyl)piperazine stage or at the final product. Alternatively the benzodioxancarboxylic acid intermediate can be resolved with an optically active base such as brucine or $\alpha_1$-phenethylamine. Other standard methods of resolution known to those skilled in the art, including but not limited to simple crystallization and chromatographic resolution, can be used. [See for example, Stereochemistry of Carbon Compounds, E. L. Eliel, McGraw Hill (1962); "Tables of Resolving Agents" Wilen and Lochmuller, *J. Chromatography* 113, 283–302 (1975).] Additionally, the optically pure (+) isomer can be prepared from the racemic mixture by enzymatic biocatalytic resolution. See for example, U.S. Pat. Nos. 5,057,427 and 5,077,217, the disclosures of which are incorporated herein by reference.

The magnitude of a prophylactic or therapeutic dose of (+) doxazosin in the acute or chronic management of disease will vary with the severity of the condition to be treated, and the route of administration. The dose, and perhaps the dose frequency, will also vary according to the age, body weight, and response of the individual patient. In general, the total daily dose range, for (+) doxazosin, for the conditions described herein, is from about 0.1 mg to about 20 mg, in single or divided doses. Preferably, a daily dose range should be between about 0.5 mg to about 10 mg, in single or divided doses, while most preferably, a daily dose range should be between about 0.5 mg to about 5 mg, in single or divided doses. In managing the patient, the therapy should be initiated at a lower dose, perhaps about 0.5 mg to about 1 mg, and increased up to about 10 mg or higher depending on the patient's global response. It is further recommended that children, and patients over 65 years, and those with impaired renal, or hepatic function, initially receive low doses, and that they be titrated based on individual response(s) and blood level(s). It may be necessary to use dosages outside these ranges in some cases, as will be apparent to those skilled in the art. Further, it is noted that the clinician or treating physician will know how and when to interrupt, adjust, or terminate therapy in conjunction with individual patient response. The terms "an amount sufficient to increase urine flow but insufficient to cause said hypotensive effects" and "an amount sufficient to lower cholesterol and LDL levels but insufficient to cause adverse effects" are encompassed by the above-described dosage amounts and dose frequency schedule.

Any suitable route of administration may be employed for providing the patient with an effective dosage of (+) doxazosin. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise (+) doxazosin as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids including inorganic and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic (mesylate), mucic, nitric, pamoic, pantothenic, phosphoric, succinic, sulfuric, tartaric, p-toluenesulfonic, and the like.

The compositions of the present invention include compositions such as suspensions, solutions, elixirs, aerosols, and solid dosage forms. Carriers such as starches, sugars, microcrystalline cellulose, diluents, granulating agents, lubricants, binders, disintegrating agents, and the like, are commonly used in the case of oral solid preparations (such as powders, capsules, and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719; the disclosures of which are hereby incorporated by reference.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 0.5 mg to about 10 mg of the active ingredient. Most preferably, the tablet, cachet or capsule contains either one of three dosages, about 0.5 mg, about 2 mg or about 8 mg of the active ingredient.

The invention is further defined by reference to the following examples describing in detail the preparation of the compositions of the present invention, as well as their utility. It will be apparent to those skilled in the art that many modifications, both to materials and methods, may be practiced without departing from the purpose and interest of this invention.

TEST 1

A test for activity in lowering serum LDL and cholesterol is carried out according to the method of Havel et al. [*Arteriosclerosis.* 2, 467–474 (1982)].

Homozygous Watanabe-heritable hyperlipidemic (WHHL) rabbits are maintained on Purina Rabbit Laboratory Chow and used at 3–5 months of age.

Blood is collected from the ear veins of unanesthetized rabbits or from the abdominal aorta of anesthetized rabbits and placed on ice. Lipoproteins are separated from plasma by sequential ultracentrifugation. For analysis of lipoprotein composition and for separation of protein components, samples are recentrifuged at their upper density limits.

Total cholesterol and triglycerides are estimated in plasma, and lipoprotein fractions by the automated technique of Rush et al. [Rush RL, Leon L, Turrell J. "Automated simultaneous cholesterol and triglyceride determination on the autoanalyzer II instrument." In: Advances in Automated Analysis-Technicon International Congress-1970/Clinical Analysis. Mt. Kisco: Futura, 1970; 1:503–507] For measurements of lipoprotein composition, one can also estimate free and esterified cholesterol, phospholipids, and protein.

TEST 2

A test for vascular dilatation is carried out as follows: New Zealand White rabbits, weighing 2.0 to 2.5 kg, are sacrificed by cervical dislocation and the thoracic aortas excised immediately. The aortas are then immersed in warm, oxygenated Krebs-bicarbonate solution and cut in transverse or spiral strips, 1 to 3 mm in width. The strips are suspended vertically in tissue baths containing an isotonic bicarbonate buffer. The composition of this buffer may be as follows (amount in millimoles per liter): NaCl, 119.0; KCl, 4.7; $CaCl_2$, 2.5; $MgSO_4$, 1.5; $KH_2PO_4$, 1.2; $NaHCO_3$, 25.0; and dextrose, 11.0. The bathing medium is aerated with 95% $O_2$ and 5% $CO_2$ and maintained at 37.0°±0.5° C. and pH 7.4. The lower end of each strip is secured to a tissue holder and the upper end attached via a string or a fine chain to a force-displacement transducer; responses are displayed on recorders. Tissues are placed under an initial tension of 0.1 to 2.0 g and permitted to stretch and equilibrate before testing. The tension on the strips is readjusted intermittently to the initial tension during the equilibration period. Drugs are introduced into the tissue baths with syringes or pipettes and removed by drainage and replacement of the bathing medium from preheated, oxygenated reservoirs. Responses are expressed as gram changes in tension above base-line.

The response of the tissue to 1 μg/mL phenylephrine is measured. The tissue is incubated with varying concentrations of the test substances and the response to phenylephrine re-evaluated. Alternatively the tissues are precontracted with an α-receptor stimulator such as phenylephrine and relaxed by gradual additions of a test substance to the bath fluid.

TEST 3

The procedure analogous to the one described above is repeated using canine urethral tissue in place of rabbit aorta to determine potential urinary tract effects.

TEST 4

A test for insulin resistance is carried out as an indication of favorable changes in serum lipid levels. Castelli, *American Heart Journal,* 112: 432–40 (1986) and McKeigne et al, *British Heart Journal,* 60: 390–96 (1988) have shown that insulin resistance and hyperinsulinemia lead to decreases in plasma HDL cholesterol concentrations and increases in plasma triglyceride levels. The beneficial effects of doxazosin on plasma lipids are therefore consistent with previous findings of a decreased insulin resistance in man after dosing with doxazosin, and a test protocol which measures insulin resistance correlates with an expectation of similar responses in serum lipids in vivo.

Insulin is a hormone that activates various biochemical processes in the body, the most well known being facilitation of glucose transport over cell membranes and activation of cell growth. The development of insulin resistance is common both in diabetics and nondiabetics, but it is only the glucose transport system that develops resistance to insulin. To compensate for the impaired glucose transport, the normal body produces more insulin and the diabetic patient has to inject higher doses of insulin. Since insulin also is a growth hormone, the increased insulin concentration induces an accelerated growth of atherosclerotic lesions and increased risk for cardiovascular morbidity and mortality.

The present studies are performed in old, spontaneously hypertensive rats (SHRs), which are known to develop insulin resistance. Racemic doxazosin, (–) doxazosin, and (+) doxazosin are studied for their effects on glucose transport, insulin plasma concentration and arterial blood pressure.

Prior to receiving vehicle or test compound, basal measurements of the following parameters are made: (1) systolic blood pressure (measured via tail cuff occlusion); (2) fasting levels of plasma insulin and triglycerides; and ( 3 ) glucose tolerance.

The SHRs receive vehicle or test compound via oral gavage once or twice daily for two or four weeks. Measurements of blood pressure, circulating insulin and triglycerides, and glucose clearance are made following two (and four) weeks of drug administration. Any changes in insulin resistance resulting from the drug treatment are evident as changes in the ratio of plasma glucose/plasma insulin levels and from the glucose tolerance tests.

TEST 5

A test for orthostatic hypotension and reflex tachycardia is carried out in dogs. Groups of dogs are tested with suitable doses of racemic doxazosin, (–) doxazosin, and (+) doxazosin and the effects on blood pressure (orthostatic hypotension) and heart rate (reflex tachycardia) are monitored and recorded at predetermined time intervals. Conscious normotensive dogs with surgically implanted arterial catheters are used to study the effects of the drugs on orthostatic hypotension and heart rate. The animals may also be equipped with cutaneous electrodes connected to suitable equipment for recording electrocardiograms. The tip of the indwelling catheter is positioned at the junction between the aorta and the left carotid artery. Blood pressure is measured by means of a pressure transducer and heart rate is computed from the systolic peaks in blood pressure or from the R-waves of the EKG. Doses of the test compounds are given orally or parenterally and the effects on the cardiovascular parameters are initially recorded with the animals in normal standing position. The animals are then held by their front paws and lifted into an upright position, standing on their hind paws. Drugs causing orthostatic hypotension will cause a sudden fall in recorded arterial blood pressure, sometimes accompanied by a reflex tachycardia.

EXAMPLE 1

ORAL FORMULATION

| | Capsules: | | |
|---|---|---|---|
| | Quantity per capsule in mg | | |
| Formula | A | B | C |
| (+) Doxazosin | 0.5 | 2.0 | 8.0 |
| Lactose | 84 | 82.5 | 76.5 |
| Cornstarch | 15 | 15 | 15 |
| Magnesium Stearate | 0.5 | 0.5 | 0.5 |
| Compression Weight | 100.0 | 100.0 | 100.0 |

The active ingredient, (+) doxazosin, is sieved and blended with the excipient. The mixture is filled into suitably sized two-piece hard gelatin capsules using suitable machinery. Other doses may be prepared by altering the fill weight and if necessary, changing the capsule size to suit.

EXAMPLE 2

ORAL FORMULATION

| | Tablets: | | |
|---|---|---|---|
| | Quantity per tablet in mg | | |
| Formula | A | B | C |
| (+) Doxazosin | 0.5 | 2.0 | 8.0 |
| Lactose | 72.25 | 70.75 | 64.75 |
| Cornstarch | 3.0 | 3.0 | 3.0 |
| Water (per thousand Tablets)* | 30.0 mL | 30.0 mL | 30.0 mL |
| Cornstarch | 18.75 | 18.75 | 18.75 |
| Magnesium Stearate | 0.50 | 0.50 | 0.50 |
| Compression Weight | 125.0 | 125.0 | 125.0 |

*The water evaporates during manufacture

The active ingredient is blended with the lactose until a uniform blend is formed. The smaller quantity of cornstarch is blended with the water to form the resulting cornstarch paste. This is then mixed with the uniform blend until a uniform wet mass is formed and the remaining cornstarch is added and mixed until uniform granules are obtained. The granules are screened through a suitable milling machine using a ¼" stainless steel screen. The milled granules are dried in a suitable drying oven and milled through a suitable milling machine again. The magnesium stearate is then blended and the resulting mixture is compressed into tablets of desired shape, thickness, hardness and disintegration.

What is claimed is:

1. A method of eliciting an increase in urine flow in a human while avoiding the concomitant liability of hypotensive effects associated with racemic doxazosin, which comprises administering to a human an amount of (+) doxazosin, or a pharmaceutically acceptable salt thereof, substantially free of its (−) stereoisomer, said amount being sufficient to increase urine flow but insufficient to cause said hypotensive effects.

2. The method of claim 1 wherein (+) doxazosin is administered by intravenous infusion, transdermal delivery, or orally as a tablet or a capsule.

3. The method of claim 2 wherein the amount of (+) doxazosin or a pharmaceutically acceptable salt thereof administered is from about 0.1 mg to about 20 mg per day.

4. The method of claim 3 wherein the amount administered is from about 0.5 mg to about 10 mg per day.

5. The method of claim 4 wherein the amount administered is from about 0.5 mg to about 5 mg per day.

6. The method of claim 1 wherein the amount of (+) doxazosin or a pharmaceutically acceptable salt thereof is greater than approximately 90% by weight of the total weight of doxazosin.

7. The method of claim 1 wherein the amount of said (+) doxazosin or a pharmaceutically acceptable salt thereof, substantially free of its (−) stereoisomer, is administered together with a pharmaceutically acceptable carrier.

8. The method according to claim 1 wherein (+) doxazosin is administered as a salt selected from the group consisting of hydrochlorides and methane sulfonates.

* * * * *